United States Patent [19]

Roteman

[11] 4,017,513

[45] Apr. 12, 1977

[54] METHOD FOR MAKING AMINOACID AMIDES

[75] Inventor: Robert Roteman, Waukegan, Ill.

[73] Assignee: Abbott Laboratories, North Chicago, Ill.

[22] Filed: Mar. 17, 1975

[21] Appl. No.: 558,581

[52] U.S. Cl. .................... 260/326.2; 260/326.45; 260/558 A; 260/561 A
[51] Int. Cl.$^2$ ...................................... C07D 207/16
[58] Field of Search ....... 260/326.2, 561 A, 558 A, 260/326.45

[56] References Cited
UNITED STATES PATENTS

| | | | |
|---|---|---|---|
| 2,790,000 | 4/1957 | Norman et al. ............... | 260/326.45 |
| 3,496,219 | 2/1970 | Young ............................. | 260/471 |
| 3,896,149 | 7/1975 | Kotone et al. ................. | 260/326.45 |
| 3,948,943 | 4/1976 | Eberhardt et al. ............ | 260/326.45 |

*Primary Examiner*—Donald G. Daus
*Assistant Examiner*—Mary C. Vaughn
*Attorney, Agent, or Firm*—Paul D. Burgauer; Robert L. Niblack

[57] ABSTRACT

The present process describes a new and improved method for making the amides of an aminoacid. The new procedure involves only two steps, produces good yield and requires neither isolation nor purification of the intermediate. It also assures that the optical rotation of the starting material is not affected.

5 Claims, No Drawings

METHOD FOR MAKING AMINOACID AMIDES

DETAILED DESCRIPTION OF THE INVENTION

In the past, numerous ways have been described for making primary or secondary amides of aminoacids from the aminoacid itself. In many of these methods, numerous steps are involved, usually requiring the method of esterifying the aminoacid initially and subsequently, removing the ester group through ammonolysis. Along with such a multistep procedure, the methods of the prior art suffer from the formation of by-products with accompanying loss in yields, and more significantly, in many instances the optical rotation of the aminoacid starting material is altered. Often, the by-products and particularly the optical isomers are very difficult to remove from the desired aminoacid amide.

It is therefore an object of the present invention to provide a process for converting an aminoacid to its amide without substantial loss of material. It is a particular object of this invention to provide a process of converting an aminoacid to a primary or secondary amide retaining the optical configuration of the starting material. It is a further object of the present invention to provide a process for producing aminoacid amides which need no or only minimal purification.

These and other objects are accomplished by the process of making an optically pure amide of an aminoacid consisting essentially in reacting the complex between the optically pure aminoacid or its ester and a cationic exchange resin in the hydrogen cycle having a $pK_a$ of $1.7 \times 10^{-5}$ to $4.0 \times 10^{-1}$ and wherein said complex contains at least one equivalent of resin per equivalent of said aminoacid with an excess of amine of the formula $RNH_2$ wherein R is hydrogen or loweralkyl, if desired in the presence of a low boiling alcohol, separating the insoluble residue from the reaction mixture, and isolating said amide from the liquid phase.

The resins suitable for the above process are any of the weak or strong cationic exchange resins that are well known by those skilled in the art. They can be made from any of the general types of polymers such as styrene, acrylic, phenolic, and others, modified to the extent of having a carboxylic or sulfonic acid group attached thereto in the range to produce the required $pK_a$ range. They also may be cross-linked to any degree and, preferably, they are used in beaded form. Examples of such resins are the Dowex, Amberlite, Duolite, Permitit or other types of resins modified in accordance with the above definition. Their particle size or bead size in their wet or swelled stage may range from 20 to 325 mesh measured by the U.S. scale.

The optically active aminoacid readily attaches to the above resin. This can be done in a batch operation whereby the resin is mixed with a solution of the aminoacids and allowed to adsorb the aminoacid or its ester, or the process can be done in a column whereby the aminoacid or aminoacid ester solution is passed through a column filled with the above cationic exchange resin in the hydrogen cycle. In both instances, the free aminoacid or its ester, the acid attaches through the carboxylic acid group to the resin, forming an ester with the defined resin. The loweralkyl esters best suited are the methyl, ethyl or propyl esters.

The desired amide can be obtained directly by treatment of the resin adsorbate with ammonia or an alkyl amine whereby the aminoacid separates directly as the desired amide, leaving the resin as an insoluble material in the solution. This cleavage reaction is substantially 100% and since the adsorption of the aminoacid to the resin essentially is without loss when there is at least one equivalent of resin present, the total yield of the new procedure is almost 100%. In addition, the optical rotation of the starting material does not change which is particularly important in the preparation of amides that are used for biologically active materials. Thus, when a pure L-aminoacid is adsorbed on a suitable resin and desorbed or cleaved therefrom by using ammonia, the pure L-amide of said aminoacid is obtained. This is generally the form needed for obtaining biologically active peptides. The products of this invention are intended to be used in the synthesis of peptides, primarily the physiologically active peptides having hormone release activities such as TRH, MIF, FSH—RH and LH—RH.

In a simple embodiment of the present process, a solution of an aminoacid in an inert solvent such as water or alcohol is agitated with at least one, preferably between 1 and 5 molar equivalents of the desired resin for several hours. This can be done at room temperature. However, where the employed resin, the aminoacid and the solvent used are heat stable, it is often indicated or even preferred to carry out this step at elevated temperatures. The reaction mixture may be filtered thereafter, although this is not necessary as ammonia gas can be introduced directly into the solution. If desired, an aqueous solution of either ammonia or of an aliphatic amine may be used in place of the gas. In case of making a secondary amide of the aminoacid, the "solution" method may be better suited while ammonia gas is well suited for making primary amides. Subsequent filtration will produce a solution of the optically pure aminoacid amide; the resin can easily be separated and is then ready for regeneration and reuse.

In order to illustrate the process of the present invention, reference is made to the following examples which, however, are not meant to limit the invention in any respect.

EXAMPLE 1

In a 360-liter stainless steel reactor, 23.6 kg. of Dowex-50-X8 resin (4.6 meq./gm.), 10 kg. of L-proline and 85 liters of methanol were refluxed with agitation for 16 - 20 hours. After that time, the mixture was cooled to 25° C. and filtered. The resin was washed with about 20 liters of methanol. The resin was then placed in a 360-liter reactor with 85 liters of methanol and gassed with 6.8 kg. of anhydrous ammonia. After completion of the ammonia addition, the reactor was sealed and agitated for 3 days, after which time the resin was filtered off and washed with 20 liters of methanol. The combined filtrate and wash liquors were evaporated to a thick syrup at 70° C. at which time 85 liters of benzene were added. Azeotropic distillation started at 57° C.; it was continued until the temperature reached 80° C. By addition of fresh benzene at occasional intervals, the reactor volume was maintained at about 60 liters. When the 80° temperature was reached, the volume was reduced to 45 liters, the slightly hazy solution was filtered through a prewarmed filter into a crystallizer which was subsequently cooled to 10° C. with agitation and kept at that temperature for 2 hours. The product was removed from the solution, dried at 55° C. It analyzed to have a rotation of $[\alpha]_D^{25}$ −96.7 (c = 2; $CH_3OH$); it melts at 97° – 100° C.

and assayed as 98.1% of optically pure L-prolinamide. The filtrate of the product medium was saved for recovery of a second crop of L-prolinamide.

EXAMPLE 2

0.2 Equivalents of L-phenylalanine and 0.2 equivalents of Dowex 50-WX8 was charged into 400 ml. of ethanol and refluxed for 10 hours with agitation. Subsequently, the reaction mixture was cooled and gassed with anhydrous ammonia. The mixture was then allowed to stand for 4 days before being filtered. The filtrate was stripped of alcohol on the Rotovac evaporator after adding 200 ml. of benzene. This was continued as in the previous example, until the 80° C. level was reached. Any unreacted L-phenylalanine was removed by filtration and the filtrate was cooled and crystallized as L-phenylalanilamide which was vacuum-dried and showed a melting point of 92° - 95° C. $[\alpha]_D^{25} + 10.8$ (c = 1, $CH_3OH$).

When in the above example, the ammonia was replaced with ethylamine the corresponding L-phenylalanine-N-Ethylamide was obtained in similar fashion and yield.

EXAMPLE 3

To a 1-liter, three-necked flask was added 29.4 g. of L-glutamic acid, 0.4 equivalents of Dowex 50-WX8 resin in the hydrogen form and 330 ml. of ethanol. After refluxing this mixture for 16 hours with agitation, the mix was cooled to room temperature and gassed with anhydrous ammonia. After standing for 5 days, the resin was filtered off and the filtrate was concentrated to about 100 ml. The concentrate was filtered in the cold and obtained crystals were washed with cold benzene and vacuum dried over night at 40° C. The crystals represented essentially 100% pure L-pyroglutamic acid amide; $[\alpha]_D^{25} -42.8°$ (c = 2; $H_2O$); producing only one spot on thin layer chromatographic plates $CHCl_3:CH_3OH:NH_4OH$ 60:45:20 and $CHCl_3:CH_3OH:CH_3COOH$ 60:40:20).

In all the above examples, both the NMR- and IR-spectra were in complete agreement with the assigned structure.

We claim:

1. The process of making the optically pure amide of an aminoacid consisting essentially in adsorbing an optically pure loweralkyl ester of an aminoacid dissolved in an inert solvent to a cationic exchange resin in the hydrogen cycle having a $pK_a$ of $1.7 \times 10^{-5} - 4.0 \times 10^{-1}$ and wherein said complex contains at least one equivalent of resin per equivalent of said aminoacid spearating the desired amide from said resin by bringing said resin in contact with an excess of an amine of the formula $RNH_2$ wherein R is hydrogen or loweralkyl, separating the insoluble residue from the reaction mixture, and isolating said amide from the liquid phase.

2. The process of claim 1 wherein said loweralkyl ester is the methyl ester.

3. The process of claim 1 wherein said R is ethyl.

4. The process of claim 1 wherein said R is hydrogen.

5. The process of claim 1 wherein said resin is being brought into contact with said amine in the prescence of methanol or ethanol.

* * * * *